United States Patent [19]

Verkaart

[11] Patent Number: 4,466,888

[45] Date of Patent: Aug. 21, 1984

[54] SUCTION LIQUID COLLECTION ASSEMBLY AND FLEXIBLE COLLECTING BAG THEREFOR

[75] Inventor: Wesley H. Verkaart, Duxbury, Mass.

[73] Assignee: Haemonetics Corporation, Braintree, Mass.

[21] Appl. No.: 266,065

[22] Filed: May 21, 1981

Related U.S. Application Data

[63] Continuation-in-part of Ser. No. 151,674, May 20, 1980, abandoned.

[51] Int. Cl.³ .............................................. B01D 35/02
[52] U.S. Cl. ..................................... 210/232; 210/927; 604/406
[58] Field of Search ............... 128/276, 272, 272.3, 128/DIG. 3, DIG. 24, 214 D; 141/8, 10, 314, 316, 379, 369, 114, 51, 54; 210/927, 232; 604/319, 322, 406, 408

[56] References Cited

U.S. PATENT DOCUMENTS

| | | | |
|---|---|---|---|
| 2,783,786 | 3/1957 | Carter | 141/314 X |
| 3,483,867 | 12/1969 | Markovitz | 210/645 X |
| 3,507,395 | 4/1970 | Bentley | 210/443 |
| 3,527,572 | 9/1970 | Urkiewicz | 210/427 X |
| 3,675,780 | 7/1972 | Marshall et al. | 210/446 |
| 3,768,653 | 10/1973 | Brumfield | 210/188 |
| 3,845,765 | 11/1974 | Ikeda | 128/277 |
| 3,863,634 | 2/1975 | Reynolds et al. | 128/276 |
| 3,866,608 | 2/1975 | Reynolds et al. | 128/276 |
| 3,965,946 | 6/1976 | D'Alo | 128/214 D |
| 3,986,506 | 10/1976 | Garber et al. | 210/927 X |
| 4,006,745 | 2/1977 | Sorenson et al. | 128/214 R |
| 4,014,329 | 3/1977 | Welch et al. | 137/205 X |
| 4,033,345 | 7/1977 | Sorenson et al. | 128/214 R |
| 4,035,304 | 7/1977 | Watanabe | 210/927 X |
| 4,047,526 | 9/1977 | Reynolds et al. | 128/214 R |
| 4,054,523 | 10/1977 | Ingenito | 210/188 |
| 4,198,972 | 4/1980 | Herb | 128/214 D |
| 4,204,537 | 5/1980 | Latham, Jr. | 128/272 X |
| 4,285,464 | 8/1981 | Latham, Jr. | 128/272 X |
| 4,306,557 | 12/1981 | Horth | 128/276 |

Primary Examiner—Frank A. Spear, Jr.
Attorney, Agent, or Firm—Hamilton, Brook, Smith & Reynolds

[57] ABSTRACT

A blood collecting bag is clamped along its peripheral edges between two shells. Inlet and outlet ports are formed in one side edge of the bag and are also clamped between the shells. The shells form a vacuum chamber around the bag with the bag serving as a sealing gasket and also house a liquid trap connected to the gas outlet from the bag. Pressure between the two shells is equalized through a vent hole formed through the bag. The bag comprises a membrane forming front and rear faces joined along peripheral edges. The disposable bag includes a laminated filter which lies flat between the front and rear faces of the bag when the bag is collapsed. The filter is sealed between the two faces of the bag along one edge thereof and is joined to the rear face of the bag along its opposite edge to define inlet and outlet chambers. Preferably, the shells are of clear plastic molded to conform to the shape of the expanded bag within the chamber.

19 Claims, 16 Drawing Figures

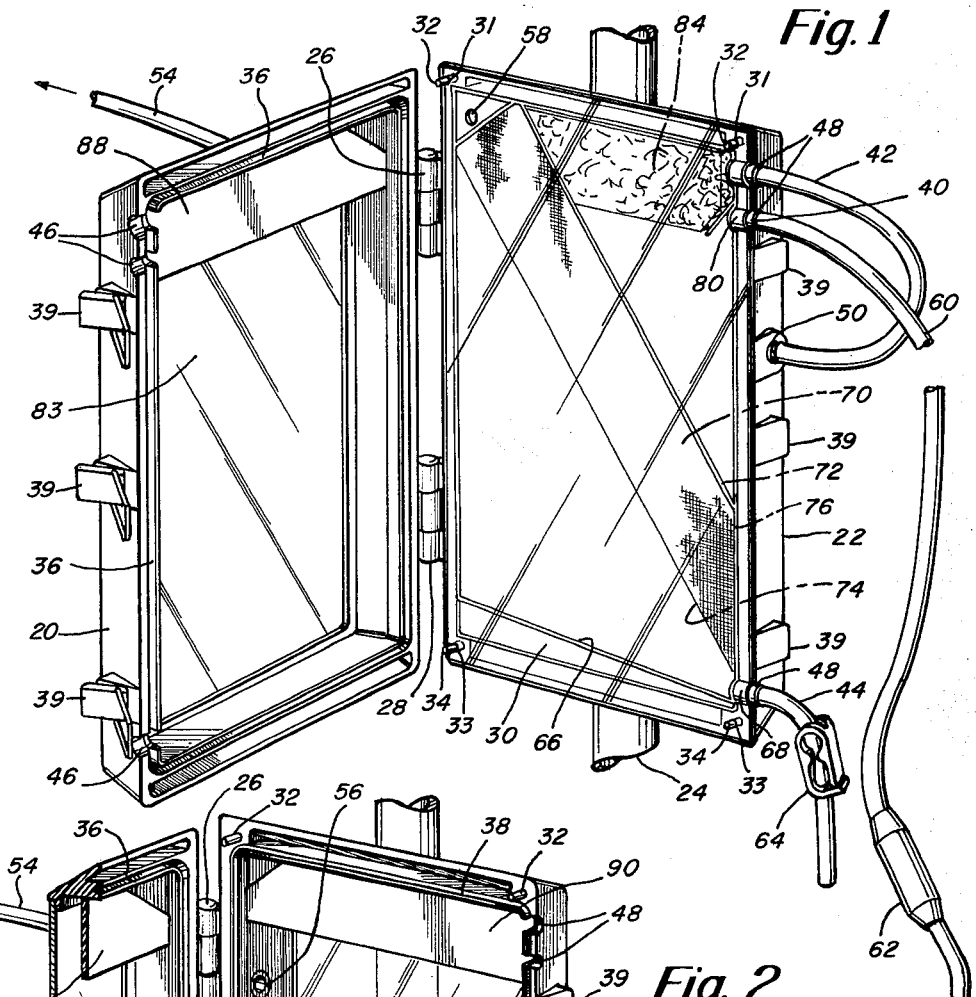
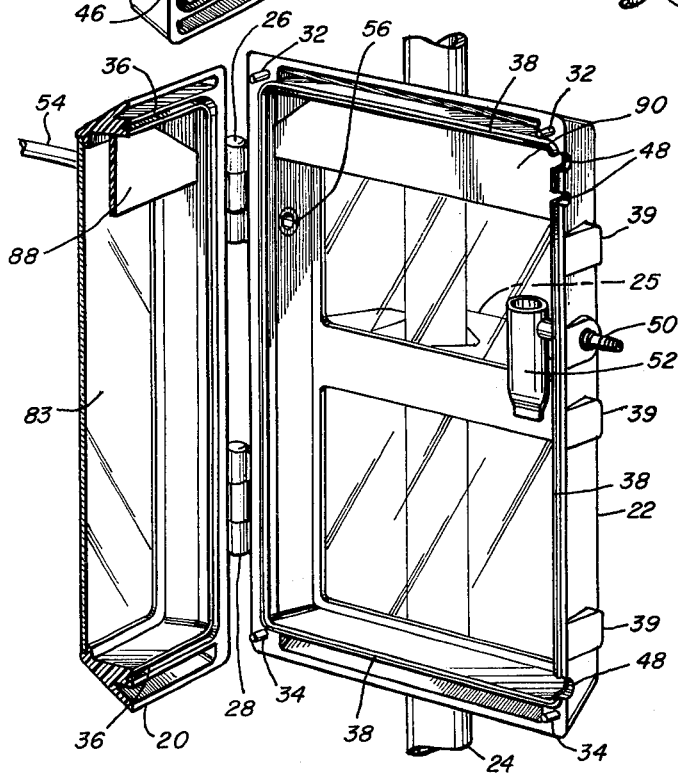
Fig. 1
Fig. 2

SUCTION LIQUID COLLECTION ASSEMBLY AND FLEXIBLE COLLECTING BAG THEREFOR

RELATED APPLICATIONS

This is a continuation-in-part of U.S. application Ser. No. 151,674, filed May 20, 1980, now abandoned, for Suction Liquid Collection Assembly and Flexible Collecting Bag Therefor.

DESCRIPTION

1. Field of the Invention

This invention relates to assemblies for collecting liquids by suction. The invention has particular application to autologous blood transfusion systems.

2. Background Art

As a patient loses blood during surgery, that blood is often replaced by transfusion to the patient. Conventionally, this requires that a supply of blood be on hand and that that blood be crossmatched with the patient's own blood to be certain that the two are compatible. The problems of processing blood from donors, of storing that blood and of crossmatching that blood with the patient are substantially circumvented by the use of autologous blood transfusion techniques. By such a technique, the patient's own blood, lost through a wound or surgical incision, is collected and returned to the patient.

The most practical means of collecting a patient's blood is by a suction wand. The thus collected blood may be contaminated by bone particles, fat, saline irrigation solutions and the like. So as not to return those contaminants to the patient, the most acceptable autologous transfusion systems clean the blood by separating out the components and contaminants in a centrifuge and washin the blood cells in that centrifuge. The washed blood cells are returned to the patient.

Prior to delivery to the cell washing system, the blood taken from the patient is collected in a reservoir. Frequently that reservoir is a transparent, rigid plastic container having a filter therein. The reservoir is connected at one end to a vacuum source and at the other end to the suction wand. The blood is collected at the bottom of the reservoir and is delivered through an outlet at the bottom. A filter element is positioned between the inlet and outlet to remove bone fragments and the like from the blood.

In order to assure the initial sterility of the reservoir, disposable rigid reservoirs are used; but the rigid containers are expensive. In an effort to avoid the expense of the rigid disposable container, several attempts have been made to use an inexpensive flexible bag as the collection reservoir. To prevent the bag from collapsing due to the suction drawn on it, the bag has been placed in a vacuum chamber held at a pressure below that in the bag.

The use of a flexible bag within a vacuum chamber leads to other problems. A primary problem has been in assuring an air tight seal to the chamber, particularly around the several inlet and outlet ports to the bag. To avoid that sealing problem one approach has been to use a cover to a vacuum canister which is integral with the disposable bag. The ports extend through that cover. In such systems the cover is disposable with the bag and is a substantial factor in the cost of the bag.

Foam can result from drawing the blood and air aspirated with the blood through a filter at the inlet to the bag and from splashing of blood introduced into a partially filled container. The foaming of the blood is a problem for at least two reasons. First, if the foam reaches an outlet to the vacuum source the vacuum source itself can be clogged or contaminated with blood. The blood carried through the outlet should be entrapped in a filter between the transfusion system and the vacuum source but such filters are not always utilized. Second, a significant problem is that the foaming action damages the blood cells and the return of those cells to the patient is counterproductive.

An object of this invention is to provide a blood collection assembly of the type in which a disposable, flexible liner is positioned within a vacuum chamber. A more particular object of this invention is to provide such an assembly in which the vacuum chamber is readily sealed despite the inlet ports to the disposable bag. A further object is to provide a bag which minimizes the amount of foaming of the blood and which also minimizes the possibility that any foam produced be taken off through the vacuum outlet.

DISCLOSURE OF THE INVENTION

To provide for proper sealing of the vacuum chamber, the liquid collection bag comprises a bag membrane forming front and rear faces joined along peripheral edges. In use the bag is clamped between rigid sheels which make up the vacuum chamber. The disposable bag thus forms a gasket between the shells. The shells also firmly hold the bag within the chamber and reinforce the bag edge seals. Preferably, ports to the disposable bag which pass through the vacuum chamber are formed at the bag edge and are also clamped by the shells. If the shells are hinged together it is advantageous for ease of bag installation and removal to have the ports extend through the edge of the bag which is located in use opposite to the shell hinges. To equalize the vacuum applied to either face of the bag within the vacuum chamber a vent hole may be provided in the bag. Support holes may be provided in the bag for supporting and correctly orienting the bag on protrusions from one of the rigid shells before the bag is clamped between them.

Preferably, the suction source, vacuum chamber and collection bag are connected in series. Suction is applied to the collection bag through the vacuum chamber. In this way the chamber is certain to be at a lower pressure than the bag and can also serve as an emergency overflow from the bag. For convenience of use and clean up, an overflow trap can be positioned within the vacuum chamber. The trap is only for use during emergency overflow and need not be sterile. Thus, it need not be formed as a part of the disposable collection bag.

A unique collection bag is provided. It incorporates a particulate material filter which divides the bag into inlet and outlet chambers. The filter lies substantially flat between the front and rear faces of the bag when the bag is collapsed. A fluid inlet port extends into the inlet chamber near the top thereof. An air outlet port is positioned along the same edge of the bag above the fluid inlet port but extends from the outlet chamber. A drain port is provided from the outlet chamber near the bottom of the bag on the same edge of the bag as the other ports. An edge of the filter element may be joined to one of the bag faces, the inlet chamber of the bag being defined at least partially by the filter and the bag face to which the filter is joined. This leaves the full height of the bag along one ede thereof clear of the filter so that filtered blood can be viewed from either side of the bag.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a perspective view of the shells of a vacuum chamber embodying this invention, hinged apart, and of a disposable bag positioned on the rear shell;

FIG. 2 is a partial perspective similar to FIG. 1 but with the disposable bag removed;

DESCRIPTION OF PREFERRED EMBODIMENTS

Figure 3:
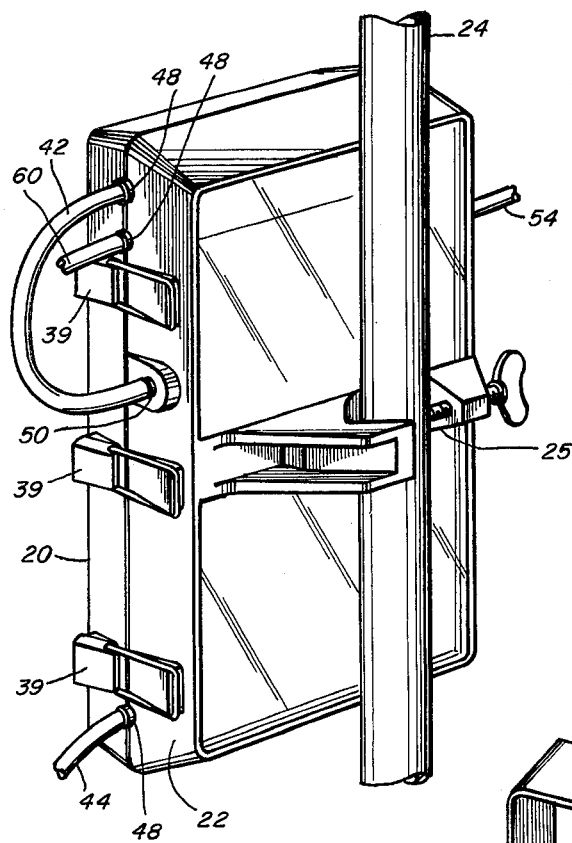
FIG. 3 is a rear view of the collection assembly with the shells closed.

A blood collection assembly embodying this invention is shown in FIGS. 1-3. A vacuum chamber includes rigid front and rear shells 20 and 22. Preferably, these shells are of formed of molded plastic such as polycarbonate. The rear shell is mounted to a pole 24 by a C-clamp 25 which is an integral part of the rear molded shell (FIG. 3). The pole 24 may extend from a centrifuge apparatus or the like or be free standing. The front shell 20 is hinged to the rear shell by hinges 26 and 28. Preferably, the hinges are loose pin or slip hinges so that the shells can be easily separated for cleaning.

A disposable, transparent, flexible blood collection bag 30 is positioned between the two shells. Preferably it is of polyvinylchloride. It includes upper support holes 31 and lower holes 33. The holes 31 and 33 may be positioned over pins 32 and 34 on the rear shell to slightly stretch the bag and to align it with the rear shell. As shown the pins face forward but they might also be positioned on the upper and lower surfaces of the rear shell directed upward and downward. Once the bag 30 is thus positioned over the rear shell the front shell is closed so that the peripheral edges of the bag are pressed between a groove 36 on one shell and a ridge 38 on the mating shell. The two shells are clamped tightly against the bag periphery by the pressure exerted by suitable clamps 39 and hinges 26 and 28. The bag is thereby held firmly in position within the vacuum chamber. The bag also advantageously serves as a gasket to the vacuum chamber, and the chamber reinforces the edge seals of the bag.

Preferably, the fluid inlet fitting 40, air outlet hose 42 and liquid drainage hose 44 extend through a side edge of the disposable bag so that they are aligned with notches 46 in the front shell and notches 48 in the rear shell. The flexible bag membrane is sealed around the fitting and hoses and serves as the gasket for them when the shells are clamped together. As a result, a tight vacuum seal is assured.

Once the bag is in place, the air outlet hose 42 is attached to a fitting 50 in the side of the rear shell. That fitting is in communication with a liquid trap 52 mounted within the rear shell (FIG. 2). The trap 52 is shown as a rigid tube, open at the top and crimped at the bottom. It might also be unitary with the molded shell or be a flexible bag having openings at the top. In the latter case, an open cell plastic foam pad or the like inside the trap bag would prevent the bag walls from sticking together. The vacuum is drawn from the rear shell by means of a vacuum line 54 attached to a fitting 56 in the shell. A one way valve is provided in the fitting 56.

In use, with the bag securely clamped between the two shells, a vacuum is drawn on the rear shell through fitting 56. The pressure in the two shells is equalized through a vent hole 58 formed through the disposable bag. This vacuum in the two shells expands the bag to its full volume. A vacuum is drawn from within the bag through the hose 42. The pressure drop through that hose is sufficient to assure that the collecting bag 30 remains expanded. Alternatively, one or more pressure regulators may be used in the system to maintain the necessary pressure differential. The vacuum in the bag draws blood through an inlet hose 60 from a wand 62 which may be held adjacent the wound or incision. The blood is collected in the bag 30, which will be discussed in detail below, and the air which enters the bag is taken off through the outlet hose 42. The bag is designed to minimize the possibility that any liquid will pass through the hose 42, but if the bag is allowed to overfill some liquid will pass out and will be collected in the trap 52. If even the trap is allowed to overfill, the blood will still be collected by the vacuum chamber. The vacuum chamber must in turn be allowed to overfill before any blood will pass through line 54.

Once a quantity of blood has been collected at the bottom of the bag 30, it is drained off through the hose 44 by opening the clamp 64. That drain hose 44 might be connected to a centrifuge blood washing apparatus. Blood can be pumped from the bag 30 through the drain tube 44 even while the system is under vacuum and blood is being collected through the wand 62.

Figure 4:
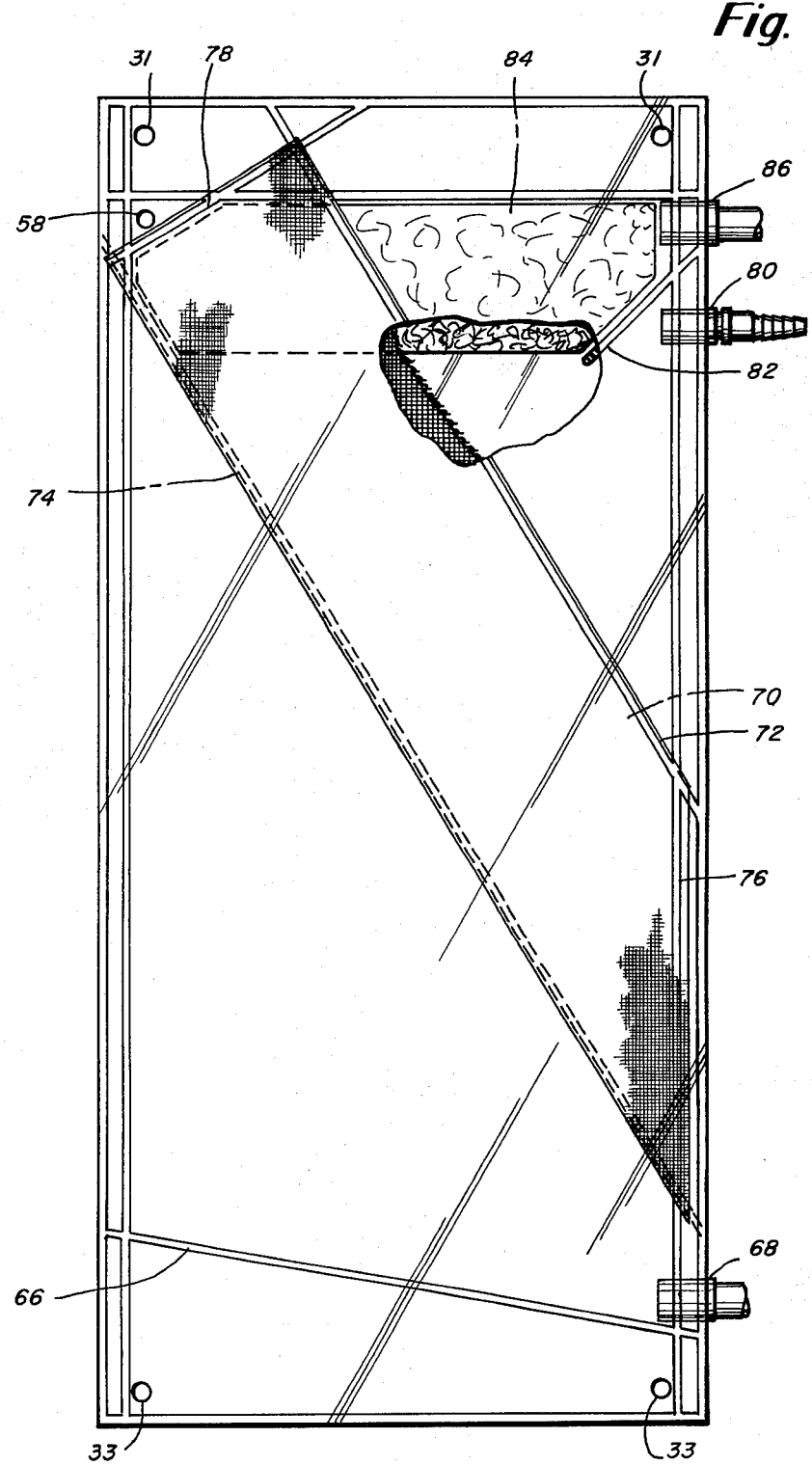
FIG. 4 is a side view of a blood collecting bag embodying this invention.
Figure 5:
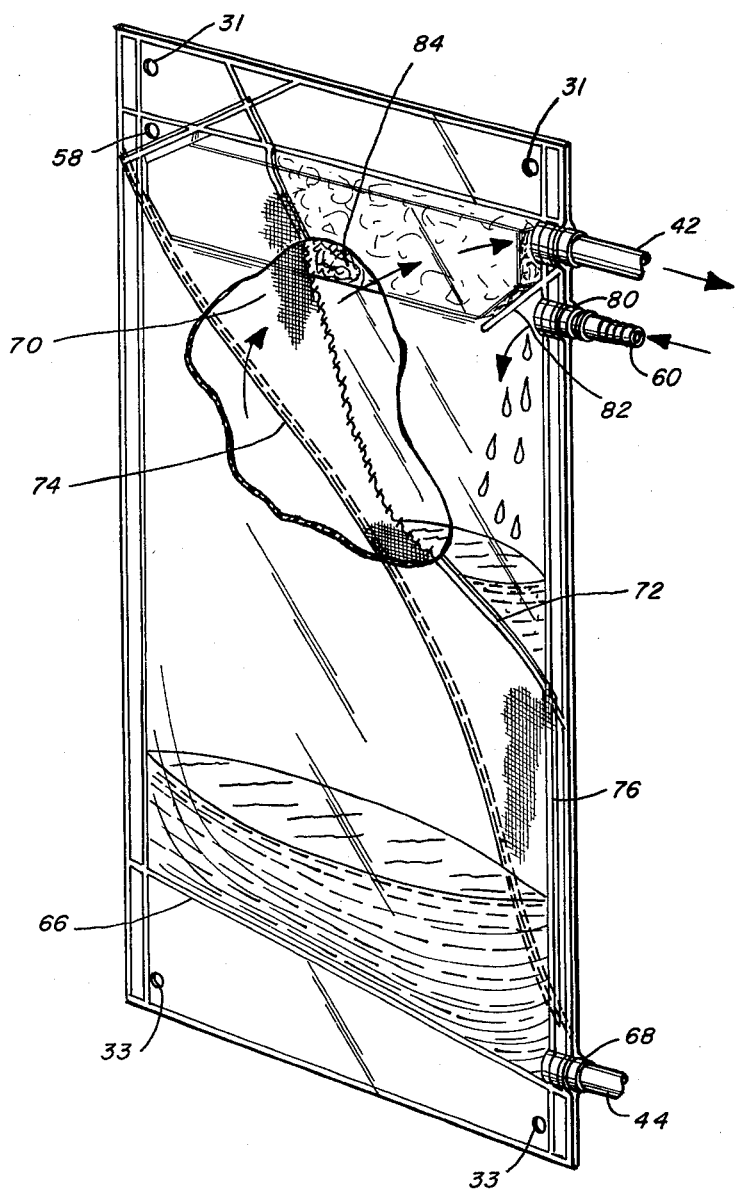
FIG. 5 is a perspective view of the bag of FIG. 4 partially filled with blood.

The disposable bag used in the assembly of FIGS. 1-3 is shown in detail in FIGS. 4 and 5. FIG. 4 is a side view of the bag and FIG. 5 shows the bag partially filled with blood.

The bag membrane includes front and rear faces sealed about a top edge, two side edges and a bottom edge as by dielectric heat sealing. Sealed edges may also result from the use of a tubular bag membrane. The bottom edge is sealed to provide a canted floor 66 to the inside of the bag in order to direct the blood toward the drainage outlet 68. A filter 70 spans the inside of the bag to filter out any particulate material which may be collected with the blood. The flexible filter 70 may, for example, be a nylon knit fabric having a 170 micron filtration diameter. The filter is heat sealed to the front face of the bag along a top edge 72 and it is heat sealed to the rear face of the bag along an edge 74. Along its lower end the filter is heat sealed between the two faces along the sealed edge 76. The seal is completed along the top edge 78. In this arrangement of the filter, a single flat layer of filter is sealed between the bag faces along the edges thereof. With only a single layer of filter between the plastic faces the strength of the heat seal is maintained. For ease in manufacturing, alternate configurations of bonding the filter to the bag faces may be used.

It should be noted that the particulate material filter 70 divides the bag into defoaming and reservoir chambers and is not located in the air path between the inlet 80 and outlet 86. In past systems where a filter is positioned across the inlet, the drawing of an air/liquid mixture through the filter has resulted in excessive foaming. With this particular arrangement the liquid is separated from the air in the region above the filter, and the liquid then passes down through the filter by gravity feed.

In this configuration, the filter lies flat when the bag is laid flat. When the bag is expanded in the vacuum chamber the filter is suspended between two faces of the bag so that there is no clinging of the filter to itself or the bag faces. The sealing of the filter along the edge 76 assures that all blood which is drained through the outlet 68 first passes through the filter to remove any particles from the blood.

Because the filter is fixed to the front face along a line 72 which is higher than the line 74 at which it is connected to the rear face, blood which flows onto the filter is directed toward the rear face. In this way, the front face is kept clean of blood so that the level of blood in the bag can be readily ascertained through a window 83 in the front shell 20 (FIG. 1). For that purpose, volume indices may be provided on the bag or window. The angle of the filter also reduces the impact of the falling liquid on the filter.

The lateral angle of the filter results from three design considerations. It is preferred that the filter be near the center of the bag to provide for a maximum filter span between the faces during bag expansion. Also, the filter must extend across the bag between the inlet port 80 and the drain port 68 to assure that all drained blood is first filtered. Finally, the reservoir chamber, which contains defoamed and filtered blood, should extend to near the defoaming pad 84 to provide a clear view of the level of collected blood; blood to the right of the filter may include foam which makes the liquid level less apparent.

The lateral angle of the filter seen in FIG. 4 also provides for a larger filter surface area and directs blood toward the right side of the bag as it flows to a pool at the bottom of the bag. With the blood thus directed to the right, the left end of the filter is kept clear so that air is easily displaced from below the filter.

The two faces of the bag are heat sealed along a line 82 at the inlet to the bag. That heat seal acts as a baffle to direct blood downward. The packing 84 is also supported by the sealed edge 74 of the filter to the rear face.

Because the two faces of the bag are brought together at the baffle seal 82, blood which enters the bag tends to contact and adhere to the faces of the bag. With the blood thus flowing along the bag faces the generation of foam is minimized. Most of the foam that is generated is broken up as the blood passes through the filter 70.

Any foam which is not broken up by the filter 70 and which reaches the level of pad 84 is broken up by pad 84 and the liquid precipitates back down into the bag. The pad 84 is supported within the bag by the baffle 82 and filter seal 74. It must be gas permeable and is preferably an open cell foam such as polyester reticulated foam. Alternatively, it may be of metal turnings, plastic mesh or the like. It may be coated with a defoaming agent such as silicone. Because very little foam actually reaches this pad 84 due to the inlet and filter construction, a negligible amount of silicone comes in contact with the collected blood.

In order to assure that all air which passes through outlet port 86 first passes through the pad 84, the vacuum chamber shells are provided with respective clamping surfaces 88 and 90 (FIGS. 1 and 2). These clamping surfaces press the bag faces against the pad 84 when the shells are clamped together.

The placement of the inlet and outlet ports 68, 80 and 86 along one side edge of the bag has several advantages. As already noted, the ports are clamped between the two shells during use in order to effect a tight seal around each of them. It is also advantageous during fabrication of the bag to have all outlets along one edge of the bag. Each of the ports 68, 80 and 86 is a segment of tubing heat sealed between two sheets which make up the front and rear faces of the bag. With all ports on one edge they can be held by a single jig during the heat sealing process and proper alignment is assured. Because the fluid inlet and gas outlet are positioned near the top of the bag and the drain outlet is positioned near the lower edge of the bag, to place the ports on a single edge they must be on one of the side edges. It is preferable that they be placed on the side edge opposite to the hinges 26 and 28 to facilitate final alignment of the ports between the shells 20 and 22.

Figure 6:
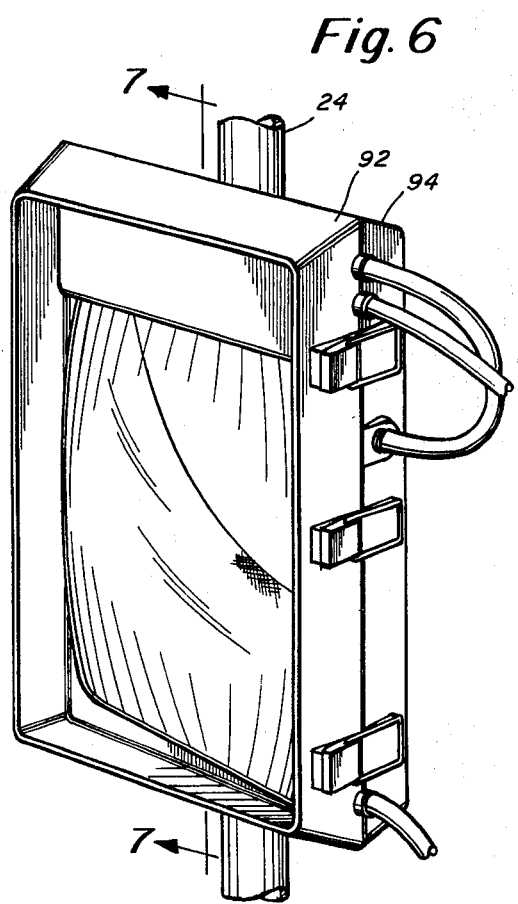
FIG. 6 is a front perspective view of an alternative embodiment of the vacuum chamber.
Figure 7:
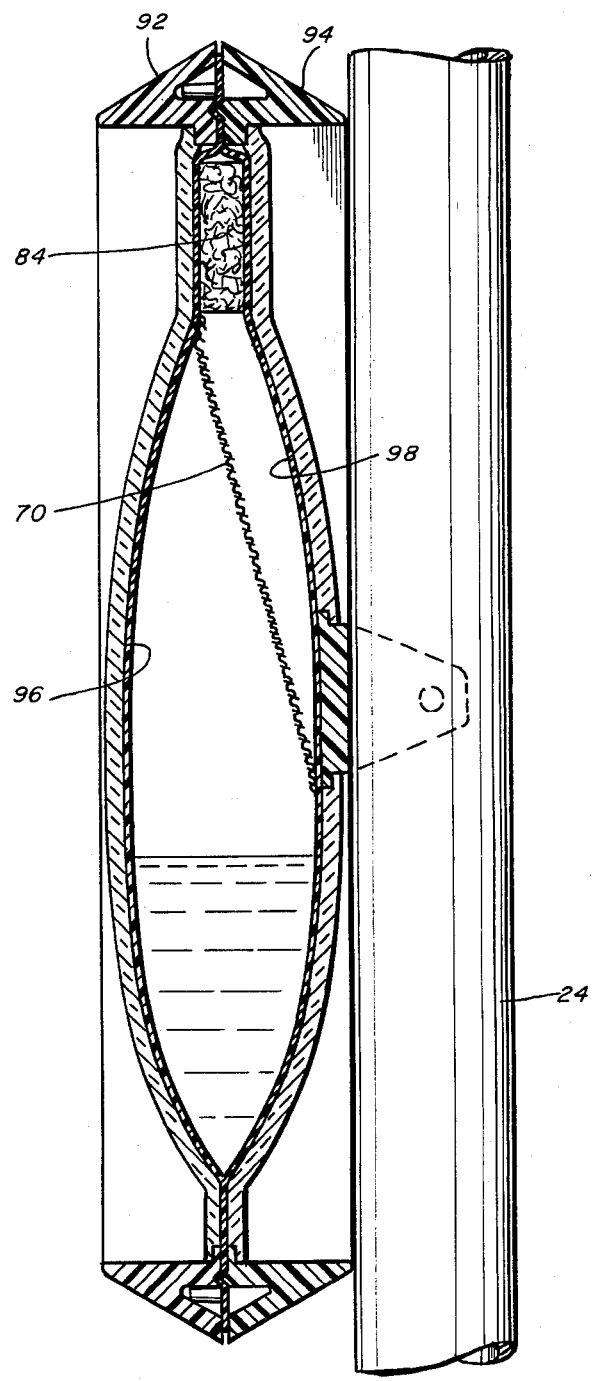
FIG. 7 is an elevational cross sectional view of the vacuum chamber of FIG. 6.

An alternative embodiment of the invention is shown in FIGS. 6 and 7. In this embodiment the faces of the shells 92 and 94 are contoured to complement the shape of the expanded bag within the vacuum chamber. The convex inner surfaces 96 and 98 of the shells support the bag against overexpansion in the event that the air outlet from the bag becomes clogged. The bag is identical to that used in the first embodiment.

Figure 8:
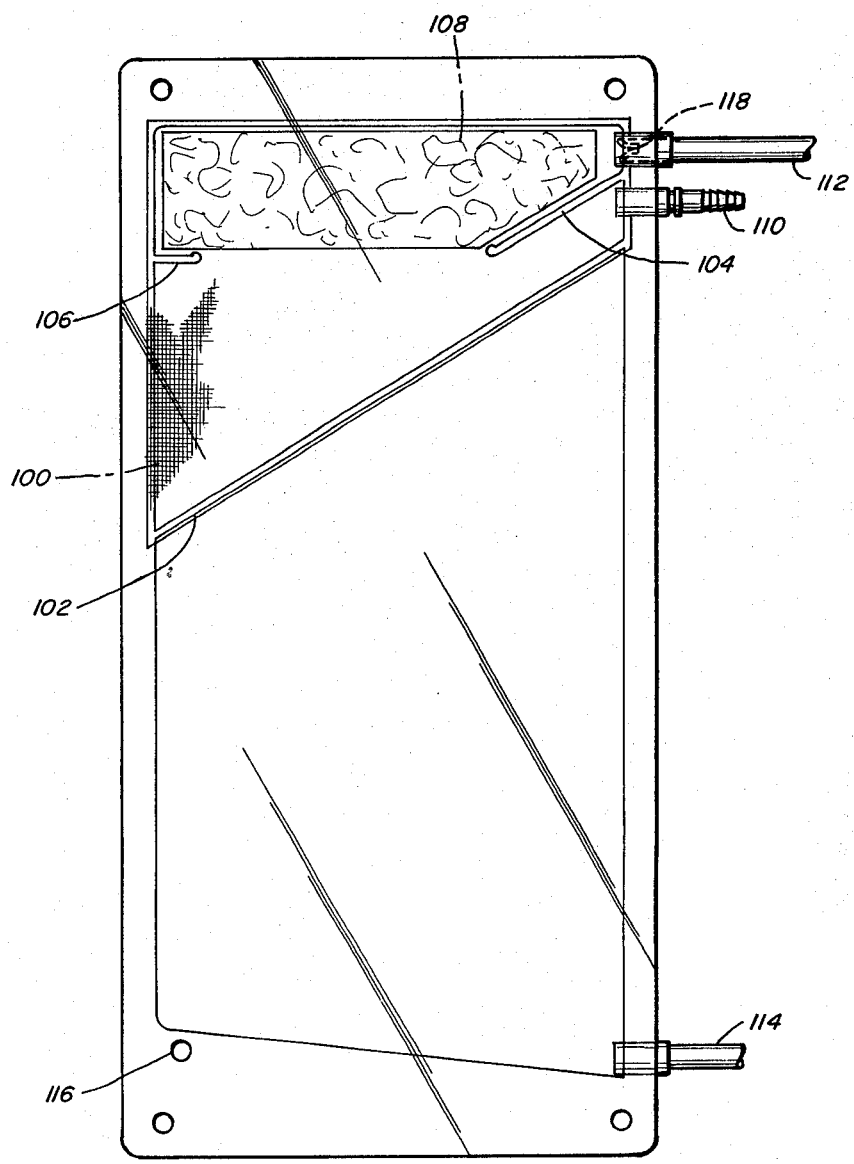
FIG. 8 is a side view of an alternative embodiment of the collection bag embodying this invention.

An alternative embodiment of the disposable collection bag suitable for use in the assembly of either FIG. 1 or FIG. 6 is shown in FIG. 8. In this embodiment, the filter screen 100 is heat sealed to the front face of the bag along a line 102. The filter is also sealed to both side edges and to the top edge of the bag between the two faces. As before, an inlet baffle 104 is formed by a heat seal between the front and rear faces of the bag. A heat seal 106 to the left of the bag provides a second support for the defoaming material 108. An inlet fitting 110 and outlet hoses 112 and 114 are provided as before. As further modifications, this embodiment includes the vent hole 116 at the lower end of the bag and a check valve 118 at the air outlet from the bag.

Figure 9:
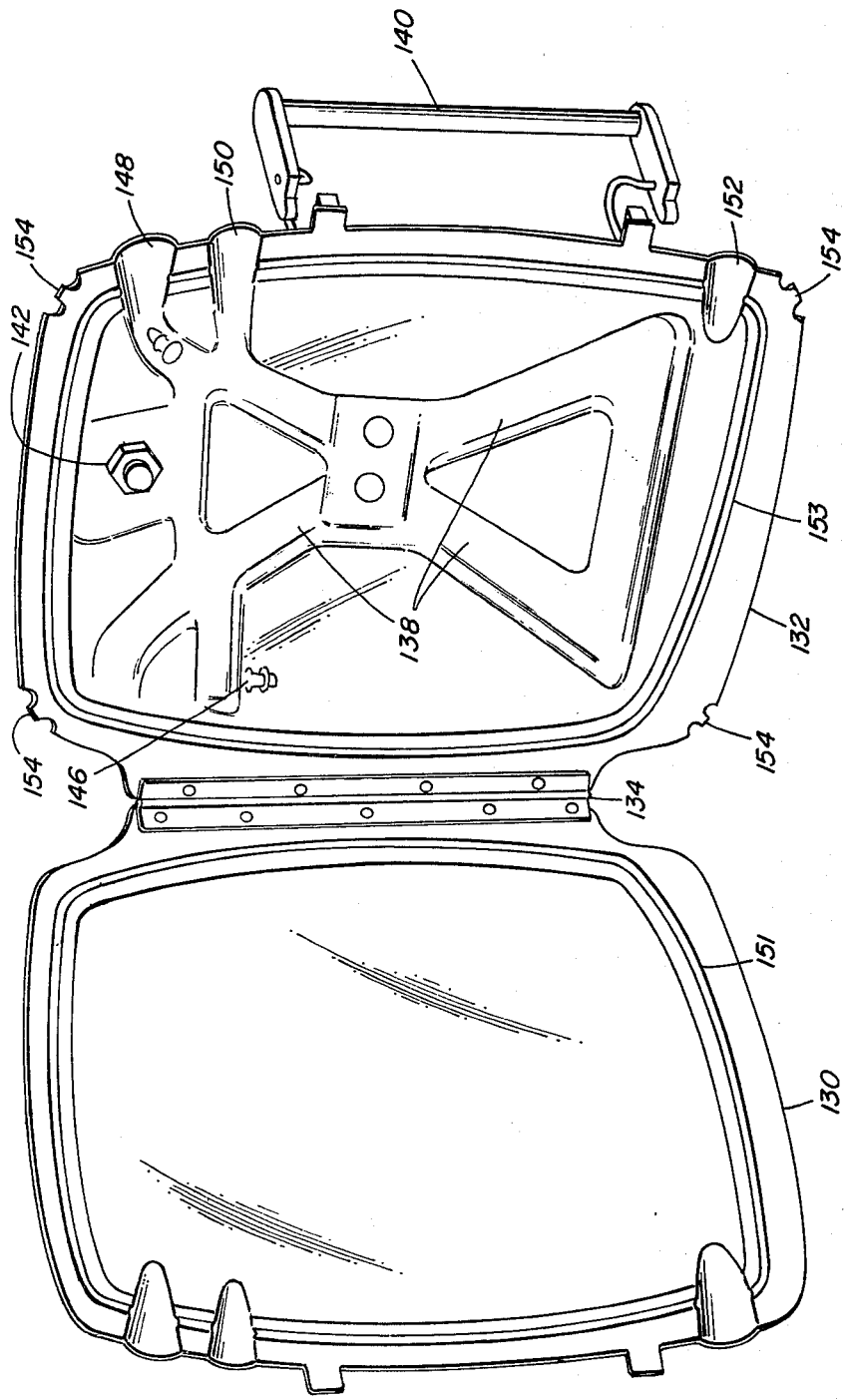
FIG. 9 is a perspecitve view of another embodiment of the vacuum chamber comprising contoured, transparent plastic shells.

FIGS. 9–16 illustrate the most recently developed embodiment of the invention. As shown in FIG. 9, the vacuum chamber is formed of two contoured, transparent, molded plastic shell 130 and 132 joined by a hinge 134. The clamp on the back of the housing, not shown, is mounted to the rear shell by screws 136. Ribs 138 are formed in the rear shell to reinforce that shell because it must support a substantial load when the bag within the vacuum chamber is filled.

The rear shell also supports a latching mechanism 140 described below. A vacuum relief valve 142 is provided on the rear to guard against excessive negative pressure. High levels of vacuum may cause damage to the cellular structure of the collected blood, and extreme vacuum levels can damage the vacuum chamber and bag. The valve may alternatively be a combination vacuum/pressure relief valve or separate vacuum and pressure relief valves.

As before, the rear shell 132 supports a port 144 to be connected to a port on the disposable bag and port 146 to be connected to a vacuum source. Each shell is formed at 148, 150 and 152 to receive the inlet and outlet ports of a disposable bag. Shell 130 is formed such that a ridge 151 is provided along the peripheral face which is to be clamped against the rear shell. And a complimentary groove 153 is formed in the rear shell 132.

Figure 10:
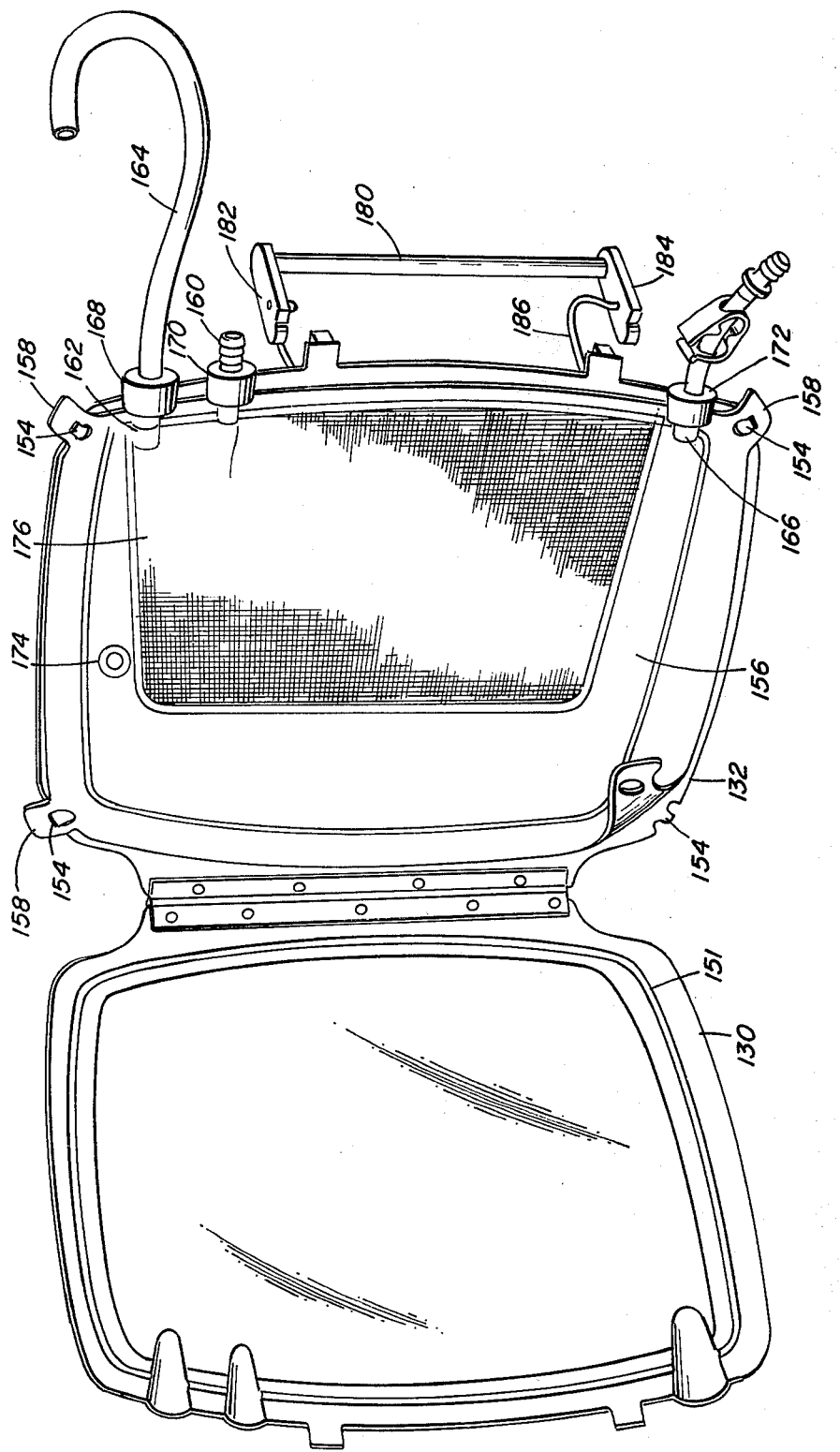
FIG. 10 is a perspective view similar to FIG. 9 but with a disposable bag positioned on the rear shell of the chamber.

Protrusions 154 are formed along the edge of the rear shell 132 at each corner thereof. As shown in FIG. 10, complimentary holes along the edge of a disposable bag 156 can be pulled over these protrusions to stretch the bag across the rear shell. Tabs 158 extend outwardly from each corner of the bag to facilitate positioning of the holes 155 over the protrusions 154.

As before, the disposable bag includes an inlet port 60, through which the air and blood mixture is drawn into the bag, near the upper end of the bag. Another port 162 is positioned just above port 160 and a hose 164 extends from that port so that it may be connected to the port 144 in the rear of the shell 132. The vacuum is drawn from the bag through that hose as before. Another port 166 is provided along the same edge of the disposable bag but at the lower end thereof for draining blood collected in the bag. The ports 160, 162 and 166 are surrounded by gaskets 168, 170 and 172 to provide for a tight vacuum seal around those ports when the two shells are clamped together.

A vent hole 174 extends through the bag, and the two faces of the bag are heat sealed around that vent hole.

Figure 11:
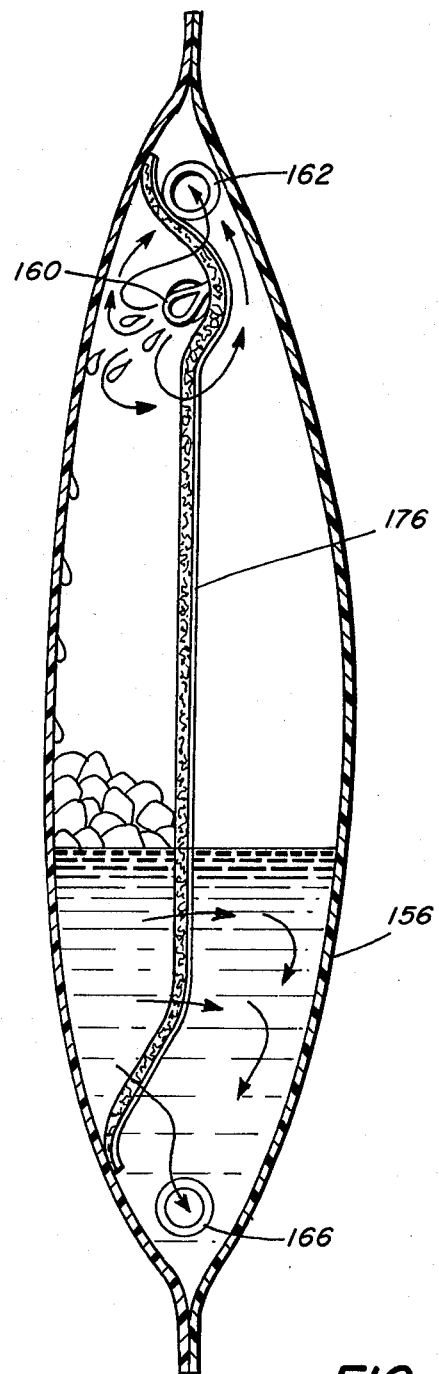
FIG. 11 is an elevational sectional view of the disposable bag of FIG. 10.
Figure 12:
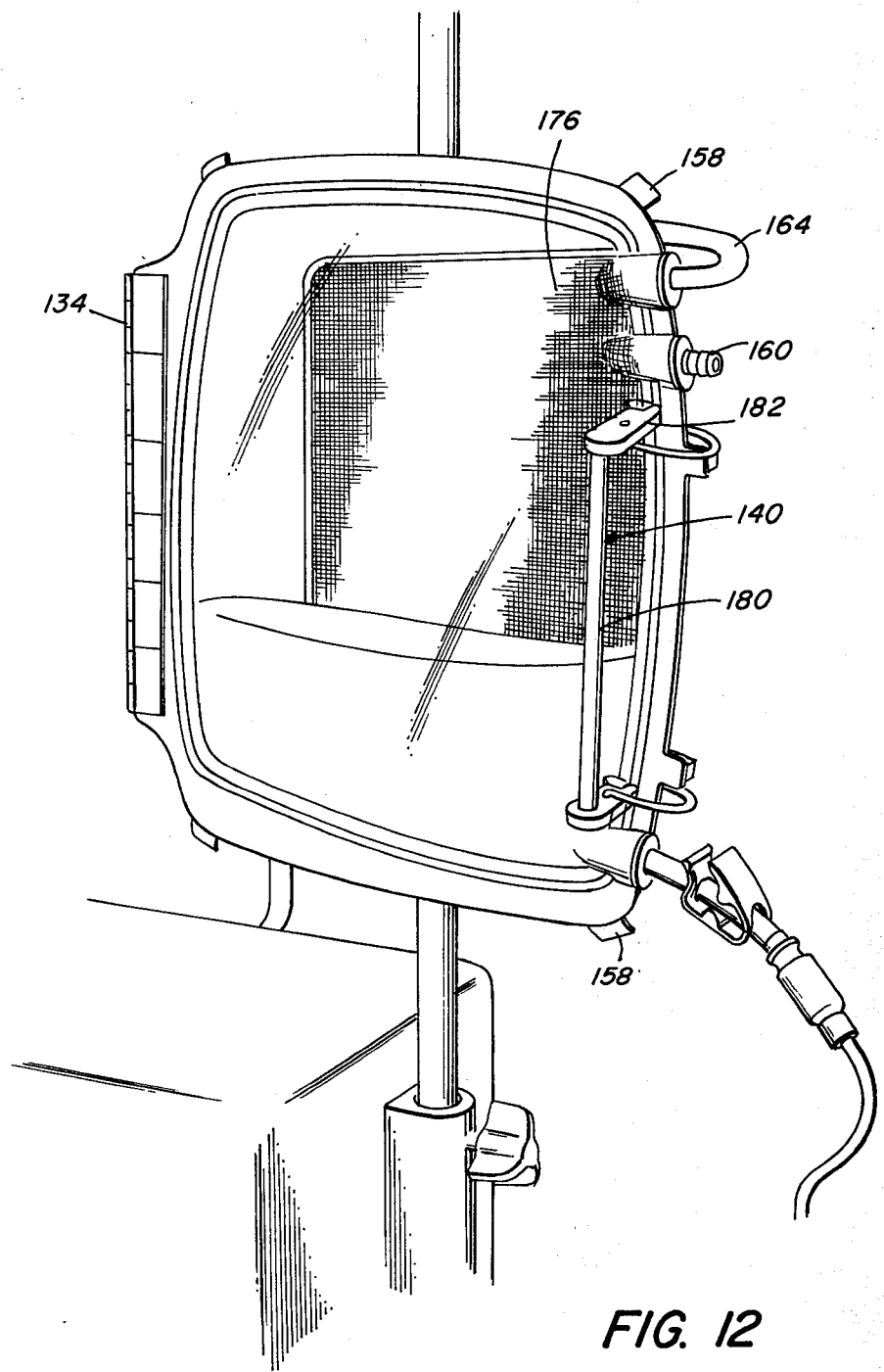
FIG. 12 is a perspective view of the vacuum chambers of FIGS. 10 and 11 closed, with the disposable bag clamped therein and partially filled with blood.
Figure 13:
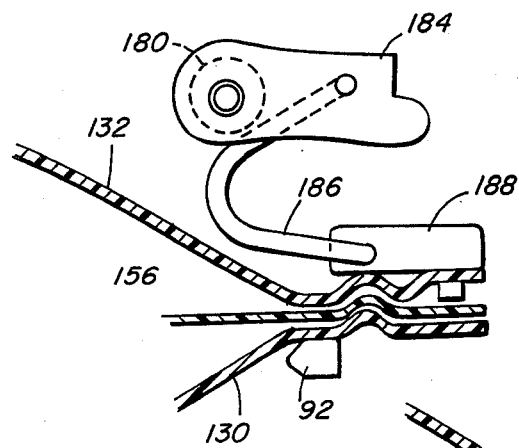
FIGS. 13-16 are partial sectional views showing operation of the latching mechanism on the vacuum chamber of FIGS. 9-12.

A filter 176, also shown in FIG. 11, is sealed between the two bag faces along the edge of the bag into which the ports extend. The filter is also sealed to the rear face of the bag along the other three filter edges. The filter thus divides the interior of the bag into two chambers, an inlet chamber behind the filter and an outlet chamber in front of the filter. The tubing which forms port 160 extends into the inlet chamber and is bent to deflect blood entering that chamber toward the rear face of the bag. The blood then flows down the rear face of the bag and is thus separated from the air which continues through the filter 176 and out the port 162 as shown in FIG. 11. Blood which collects at the bottom of the bag must flow through the filter 176 as shown in FIG. 11 before it is drained through the port 166.

The filter 176 acts to break up foam and collect particles in the blood. Preferably, it is a two layer laminate with a large pore filter of about 280 microns facing the inlet chamber and a finer pore filter of about 180 microns facing the outlet chamber. The use of the coarse filter minimizes clogging of the finer filter. The filter 176 may be a lamination of open cell plastic foam of different pore sizes, a foam and fabric lamination or any other suitable lamination. Although less desirable, a single stage filter may be used, or three or more stages may be used. A silicone defoamer permeates the filter.

Because the filter is joined to the rear face of the bag, the filter does not extend to the far left edge of the bag as viewed in FIG. 10. That region of the bag is left clear of the filter so that the level of filtered blood can be more clearly observed. To be certain that that clear region is free of foam which would make a reading of the liquid level difficult, the inlet chamber is that chamber between the filter and the bag face to which the filter is joined.

A more significant benefit of sealing the filter to the rear face is that the filter is thus prevented from being drawn against the front face of the bag. If the filter were sealed to the entire periphery of the bag, the lower pressure in the outlet chamber would draw the filter toward that face of the bag, and the outlet chamber would be reduced to virtually no volume at all. With the filter sealed to the rear face, it is pulled by that face from the front face to assure two volumes.

With the disposable bag mounted to the rear shell, the front shell is closed against the rear with the periphery of the disposable bag 156 forming a gasket between the two shells. An overcenter latching mechanism having a handle 180 mounted to the rear shell seves to clamp the two shells together as shown in FIGS. 13-16. Those figures show an end view of the latching mechanism. The mechanism comprises cams 182 and 184 joined by the handle 180 and a shaped rod 186. The rod 186 is mounted to the rear of the rear shell 132 for rotation about a vertical axis. To that end, it extends through a bearing block 188 at each end of the rod.

Figure 14:
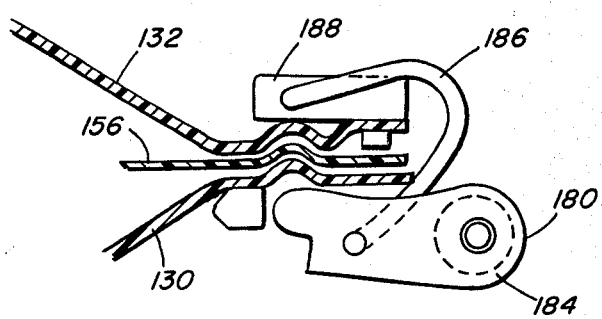
Figure 15:
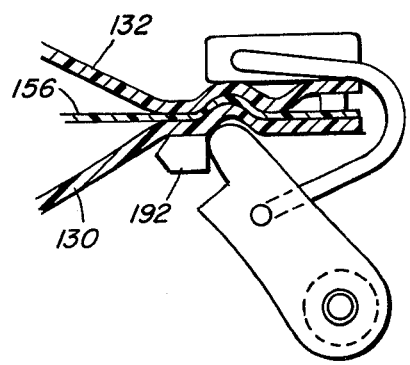
Figure 16:
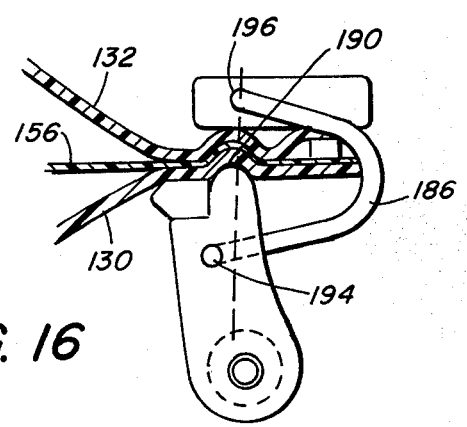

When the vacuum chamber is open for loading or unloading of a disposable bag, the cams 182 and 184 and the handle 180 can be pivoted back behind the rear shell where they are out of the way of the user. With the disposable bag mounted to the protrusions 154 of the rear shell, the front shell 130 can be closed as shown in FIG. 14 with the ridge 151 pressing the periphery of the bag 156 into the groove 153. The handle 18 is then grasped and pulled toward the front of the vacuum chamber with the rod 186 swinging around the outer edge of the two shells as shown in FIG. 14. The handle is then pressed to the left so that the cam pivots in a groove 190 opposite to the ridge 151 and then presses the two shells together. The cams are stopped by stops 192 once the pivot axis 194 of rod 186 in cams 182 and 184 passes the center line which extends through the rotational axis 196 and the effective pivot point 198 of the cam against the shell. With the cam/rod pivot axis 194 beyond that center line, the cam is locked into its latching position. The latch can be readily released by pressing the handle 180 back to the right.

Although not shown in the final embodiment, a liquid trap may be provided in the rear shell, and a one-way valve may be provided in the system.

While the invention has been particularly shown and described with reference to preferred embodiments thereof, it will be understood by those skilled in the art that various changes in form and details may be made therein without departing from the spirit and scope of the invention as defined by the appended claims. Further, the invention may be used in systems for collecting liquids other than blood.

I claim:

1. A suction liquid collection assembly of the type having a flexible, impervious liquid collection bag associated with a vacuum chamber, the bag including a fluid inlet port near the top of the bag, an outlet port near the top of the bag to which a vacuum source is connectable to draw liquid and air through the inlet port into the collection bag, and a drain port at the bottom of the bag, the improvement of:

the liquid collection bag comprising a bag membrane forming front and rear bag faces joined along peripheral edges with the fluid inlet port, the outlet port and the drain port passing through a single side edge of the bag;

the vacuum chamber comprising at least two shells hinged together at a vertical side edge; and in an operating arrangement, the bag periphery being securely clamped between the shells along the entire bag periphery such that the bag periphery forms a gas sealing gasket between the shells, with the fluid inlet port, outlet port and drain port clamped between the shells along a side edge opposite to the side edge at which the shells are hinged, a vacuum being drawn from the bag through the outlet port and a greater vacuum being drawn from the vacuum chamber on each face of the bag.

2. A suction liquid collection assembly as claimed in claim 1 wherein the inside surfaces of the shells are shaped to conform to the liquid collection bag expanded within the vacuum chamber.

3. A suction liquid collection assembly as claimed in claim 1 including a vent hole through the bag for equalizing the pressure on each face of the bag.

4. A suction liquid collection assembly as claimed in claim 1 including support holes in the bag and complementary protrusions on one of the shells for orienting and supporting the bag before it is clamped between the shells.

5. A suction liquid collection assembly as claimed in claim 1 wherein the liquid collection bag includes a filter element within the bag which divides the bag into inlet and outlet chambers, the filter element lying substantially flat between front and rear faces of the bag when the bag is collapsed, there being a fluid inlet port into the inlet chamber near the top thereof, an air outlet port from the outlet chamber near the top thereof and a drain port from the outlet chamber near the bottom thereof.

6. A suction liquid collection assembly as claimed in claim 5 wherein an edge of the filter element is joined to one of the bag faces away from the peripheral edges at the bottom and one side of the bag, the filter and the bag face to which the filter is joined forming walls of both the inlet and outlet chambers, and the outlet chamber extends from about the bottom of the bag to about the highest fill level of the bag.

7. A suction liquid collection assembly as claimed in claim 5 or 6 wherein the filter is a lamination of at least two filter layers of different pore sizes.

8. A suction liquid collection assembly as claimed in claim 1 wherein the suction is drawn from the bag through the vacuum chamber.

9. A suction liquid collection assembly as claimed in claim 1 wherein the vacuum chamber comprises two shells, one shell having a ridge along its periphery and the other shell having a complementary groove, and the bag is securely clamped between the shells along the bag periphery between the ridge and complementary groove to form a gasket between the shells.

10. A flexible liquid collection bag suitable for use in a suction blood collection system comprising:

a bag membrane forming front and rear bag faces joined alongside, top and bottom peripheral edges such that the membrane may be clamped between rigid pressure shell components;

fluid inlet and air outlet ports formed near the top of the bag, each through an edge thereof, and a drain port formed near the bottom of the bag through an edge thereof;

a filter element within the bag which divides the bag into inlet and outlet chambers, the filter element lying substantially flat between front and rear faces of the bag when the bag is collapsed, the fluid inlet port passing into the inlet chamber near the top thereof, the air outlet port passing from the outlet chamber near the top thereof and the drain port passing from the outlet chamber near the bottom thereof; and a vent hole through the bag membrane for equalizing pressure applied to the bag faces.

11. A liquid collection bag as claimed in claim 10 wherein the inlet, outlet and drain ports extend into the respective chambers through a single edge of the bag.

12. A liquid collection bag as claimed in claim 10 wherein an edge of the filter element is joined to one of the bag faces away from the peripheral edges at the bottom and one side of the bag, the filter and the bag face to which the filter is joined forming walls of both the inlet and outlet chambers, and the outlet chamber extends from about the bottom of the bag to about the highest fill level of the bag.

13. A liquid collection bag as claimed in claim 10 wherein the filter is a lamination of at least two filter layers of different pore sizes.

14. A liquid collection bag as claimed in claim 10 including support holes at the four corners thereof.

15. A suction liquid collection assembly of the type having a flexible, impervious liquid collection bag associated with a vacuum chamber, the bag including a fluid inlet port at about the top of the bag, an outlet port at about the top of the bag to which a vacuum source is connectable to draw liquid and air through the inlet port into the collection bag, and a drain port at the bottom of the bag, the improvement of:

the liquid collection bag comprising a bag membrane forming front and rear bag faces joined along peripheral edges with the fluid inlet port, the outlet port and the drain port each passing through the peripheral edges of the bag;

the vacuum chamber comprising at least two shells hinged together at an edge; and in an operating arrangement, the bag periphery being securely clamped between the shells along the entire bag periphery such that the bag periphery forms a gas sealing gasket between the shells, with the fluid inlet port, outlet port and drain port clamped between the shells, a vacuum being drawn from the vacuum chamber on each face of the bag.

16. A suction liquid collection assembly as claimed in claim 15 wherein the inside surfaces of the shells are shaped to conform to the liquid collection bag expanded within the vacuum chamber.

17. A suction liquid collection assembly as claimed in claim 15 including a vent hole through the bag for equalizing the pressure on each face of the bag.

18. A suction liquid collection assembly as claimed in claim 15 wherein the liquid collection bag includes a filter element within the bag which divides the bag into inlet and outlet chambers, the filter element lying substantially flat between front and rear faces of the bag when the bag is collapsed, there being a fluid inlet port into the inlet chamber near the top thereof, an air outlet port from the outlet chamber near the top thereof and a drain port from the outlet chamber near the bottom thereof.

19. A suction liquid collection assembly as claimed in claim 18 wherein an edge of the filter element is joined to one of the bag faces away from the peripheral edges at the bottom and one side of the bag, the filter and the bag face to which the filter is joined forming walls of both the inlet and outlet chambers, and the outlet chamber extends from about the bottom of the bag to about the highest fill level of the bag.

* * * * *